United States Patent
Goughnour et al.

[19]

[11] Patent Number: 6,017,105
[45] Date of Patent: Jan. 25, 2000

[54] HORIZONTAL SLIDING DOOR GUIDANCE METHOD

[75] Inventors: Jeffrey A. Goughnour; Gary L. Anderson, both of Erie, Pa.

[73] Assignee: Steris Corporation, Mentor, Ohio

[21] Appl. No.: 09/185,430

[22] Filed: Nov. 3, 1998

[51] Int. Cl.$^7$ .................................................. A47B 81/00
[52] U.S. Cl. ........................... 312/209; 312/296; 49/209; 49/212
[58] Field of Search ..................... 312/209, 296, 312/304, 334.23, 334.24, 334.27, 334.28; 49/209, 211, 212, 213, 276, 423

[56] References Cited

U.S. PATENT DOCUMENTS

| | | | |
|---|---|---|---|
| 849,291 | 4/1907 | Van Slyke | 49/212 |
| 1,925,473 | 9/1933 | Willard | 49/213 |
| 2,807,836 | 10/1957 | Knowles | 49/212 |
| 2,815,203 | 12/1957 | Coors | 49/212 |
| 3,660,936 | 5/1972 | Bryson | 49/209 |
| 3,912,348 | 10/1975 | Seymour | 312/296 X |
| 4,495,729 | 1/1985 | Britzke et al. | 49/212 |
| 4,880,046 | 11/1989 | Gesy | 49/212 X |
| 4,930,256 | 6/1990 | Kawanishi et al. | 49/209 |
| 4,936,049 | 6/1990 | Hansen | 49/209 |
| 5,050,943 | 9/1991 | Barnett | 312/209 X |
| 5,237,777 | 8/1993 | Houston et al. . | |
| 5,239,781 | 8/1993 | Napierkowski et al. . | |
| 5,249,392 | 10/1993 | Houston et al. . | |

*Primary Examiner*—Peter M. Cuomo
*Assistant Examiner*—Hanh V. Tran
*Attorney, Agent, or Firm*—Fay, Sharpe, Fagan, Minnich & McKee, LLP

[57] ABSTRACT

A guidance assembly (28) guides a door (22) to a cabinet (10) while it is moved between an open position, in which access to an interior chamber is provided through an opening (16) in the cabinet, and a closed position, in which the door covers the opening. The guidance system includes four pairs of rollers (32, 34) which are mounted to upper and lower horizontal sides of the door. The rollers roll along upper and lower horizontal tracks (38, 42) which are mounted to an exterior wall (18) of the cabinet, adjacent upper and lower ends of the opening. Leading and trailing recesses (56, 62) are defined in the tracks to receive the rollers when the door is in the closed position. Leading pairs (32) of the rollers have shorter shafts (52) than corresponding trailing pairs (34) of the rollers. The trailing recesses (62) are further from the door than the leading recesses (56), leaving a narrow strip of land (64) between the trailing recesses and the door. The leading rollers engage these strips of land while the door is moving between open and closed positions. This maintains a space between the door and the cabinet during opening and closing the door which prevents damage to the door and the exterior wall of the cabinet and to a sealing member (46) disposed between the door and the cabinet. Flanges (78,80,82,84) on four sides of the door engage retaining members (38,42,91,94) when the seal is activated to limit outward movement of the door. The upper and lower tracks provide the retaining members for the upper and lower horizontal sides of the door. As the door moves outward, inner rollers of each pair of rollers enter the corresponding recesses, thereby avoiding stress on the rollers.

22 Claims, 8 Drawing Sheets

HORIZONTAL SLIDING DOOR GUIDANCE METHOD

The present invention relates to the door closure arts. It finds particular application in conjunction with a horizontal sliding door for sealing the opening to a sterilization chamber and will be described with particular reference thereto. It should be appreciated, however, that the invention is also applicable to a wide variety of other closure systems.

In many applications, it is desirable to have a chamber door sealingly engage a chamber opening. A gasket, positioned between the door and the outside of the chamber, creates an airtight seal between the door and chamber opening. For large chambers, such as walk-in steam sterilizers, horizontal sliding doors are sometimes used to allow the door to be moved from the open to the closed position with a minimum of force. During translation, the door is guided to minimize scraping of the front of the chamber and destroying of the seal. When closed, the door is provided with some freedom of axial movement so that the door is able to move a small amount as the pressure changes inside the sterilizer. Without this slack, the movement of the door would place stresses on the guidance system, leading to premature failure.

To provide this axial movement, the guidance system commonly includes a combination of rollers and recessed tracks. Unique bracketing is often needed to mount the rollers and unique tracks are generally provided which have the sole purpose of guidance. Additionally, because of the recesses, the guidance system does not provide guidance, and thus seal protection, for the entire door translation.

The present invention provides for a new and improved guidance method for a horizontal sliding door which overcomes the above-referenced problems and others.

SUMMARY OF THE INVENTION

In accordance with one aspect of the present invention, a sterilization or disinfection apparatus is provided. The apparatus includes a housing which defines an interior chamber and an opening. A door has an interior face sized to seal the opening, an outer face, a leading edge, a trailing edge, and a pair of opposite sides. A guidance assembly guides the door between an open position, in which items to be sterilized or disinfected are capable of being loaded into the chamber, and a closed position, in which the door covers the opening. The guidance assembly includes sets of leading and trailing rollers rotatably mounted to the door by shaft portions of each of the rollers. Shaft portions of either the leading or trailing rollers are longer than the other. The rollers engage first and second tracks which are mounted adjacent the door. Recesses are defined in outer surfaces of the tracks for receiving outer rollers when the door is in the closed position.

In accordance with another aspect of the present invention, a system for guiding a door horizontally between an open position and a closed position, in which a chamber opening is sealed is provided. The system includes two leading rollers rotatably mounted to the door by shaft portions of each of the leading rollers adjacent a leading edge of the door, an upper leading roller of the two leading rollers mounted to an upper surface of the door and a lower leading roller of the two leading rollers mounted to a lower surface of the door. Two trailing rollers are correspondingly rotatably mounted to the door adjacent a trailing edge of the door. The shaft portion of one of the upper trailing roller and the upper leading roller is longer than that of the other. The shaft portion of one of the lower trailing roller and the lower leading roller is longer than that of the other. Upper and lower tracks are mounted adjacent upper and lower peripheral edges of the opening. The upper rollers engage the upper track and the lower rollers engage the lower track. Leading and trailing recesses are defined in the tracks for receiving the leading and trailing rollers, respectively, when the door is in a closed position. The trailing recesses are vertically positioned such that the leading rollers do not enter the corresponding trailing recess as the door is moved between the open position and the closed position.

In accordance with a still further aspect of the present invention, a method of guiding a sliding door between an open position, in which access is provided to the interior of a steam cabinet through an opening defined in the cabinet, and a closed position, in which the opening is covered by the door, is provided. The method includes rolling upper and lower leading and trailing rollers which are rotatably connected to the door adjacent to upper and lower leading and trailing ends of the door, respectively, along outer surfaces of horizontal upper and lower tracks until the upper and lower leading rollers engage leading recesses defined in the outer surface of the upper and lower tracks and the upper and lower trailing rollers engage trailing recesses defined in the outer surface of the upper and lower tracks. The method includes rolling the upper and lower leading rollers across strips of land defined by the outer surfaces of the upper and lower tracks adjacent the trailing recesses, the strips of land engaging a portion of the leading rollers so that the leading rollers are not received by the trailing recesses.

In accordance with a yet further aspect of the present invention, a method of sealing a chamber opening is provided. The method includes guiding a door from an open position, in which access to the opening is provided, to a closed position, in which the door covers the opening. The guiding step of the method includes rolling upper and lower leading and trailing rollers which are rotatably connected to the door adjacent to upper and lower leading and trailing ends of the door, respectively along outer surfaces of horizontal upper and lower tracks until the leading rollers engage leading recesses defined in the outer surfaces of the upper and lower tracks, respectively, and the trailing rollers engage trailing recesses defined in the outer surfaces of the upper and lower tracks. The rolling step includes rolling the leading rollers across strips of land defined by the outer surfaces of the upper and lower tracks adjacent the trailing recesses, the strips of land engaging a portion of the leading rollers so that the leading rollers are not received by the trailing recesses. The method further includes engaging a first flange on an upper surface of the door with an inner surface of the upper track, engaging a second flange on a lower surface of the door with a rear surface of the lower track, and activating a seal to seal the door to the periphery of the opening.

One advantage of the present invention is that the door is fully guided along the entire length of its travel.

Another advantage of the present invention is that the guidance system provides axial translation for pressure load reversals within the sterilizer.

Another advantage of the present invention is that the guidance system allows the door to be used in either a left-to-right or right-to-left sliding mode with a minimum of alteration to the door.

Still further advantages of the present invention will become apparent to those of ordinary skill in the art upon reading and understanding the following detailed description of the preferred embodiment.

BRIEF DESCRIPTION OF THE DRAWINGS

The invention may take form in various components and arrangement of components and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
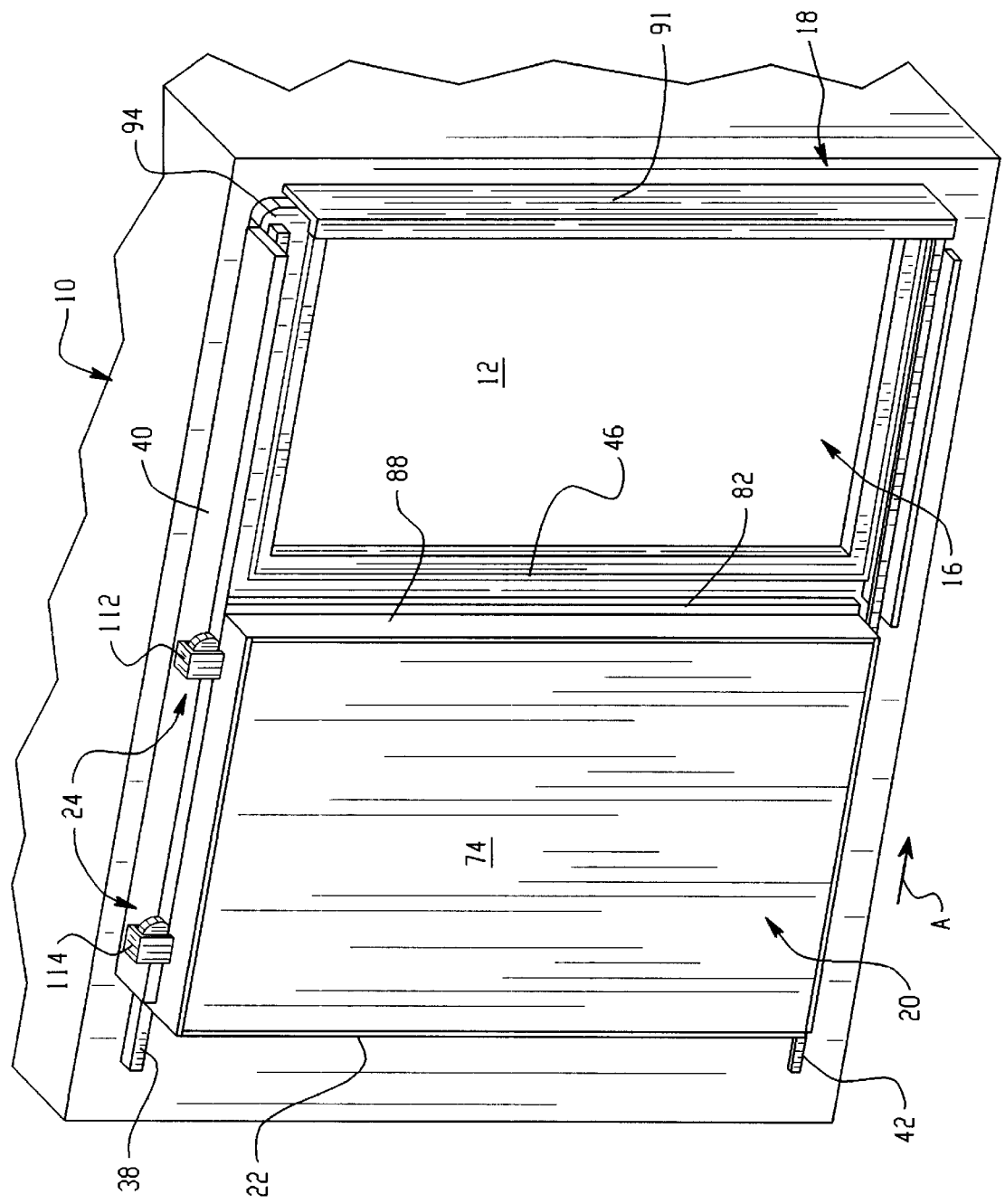
FIG. 1 is a front perspective view of a walk-in steam sterilizer with a horizontal sliding door in the open position, in accordance with the present invention.
Figure 2:
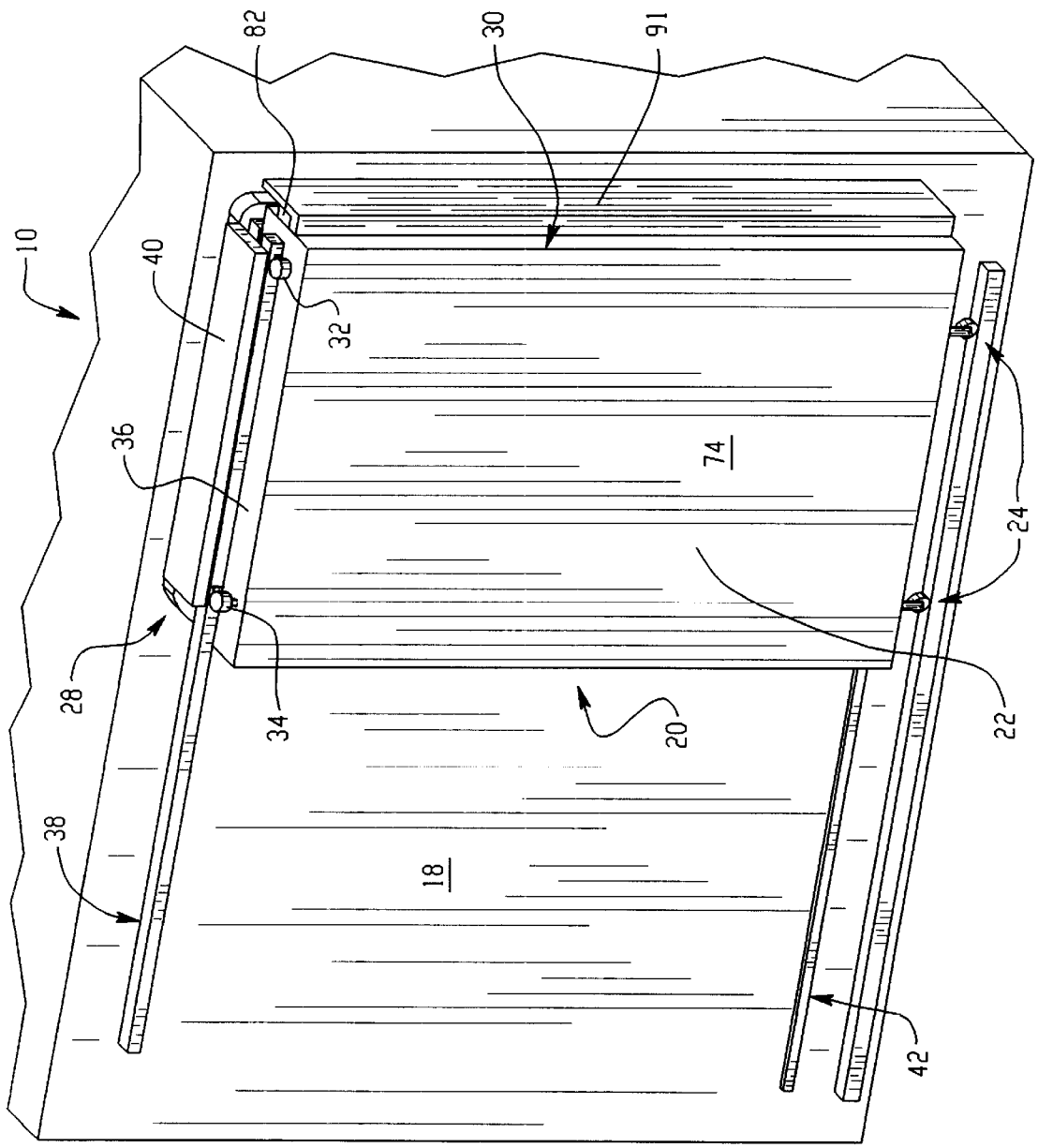
FIG. 2 is a front perspective view of another embodiment of the walk-in sterilizer with the door in the closed position, in accordance with the present invention.

With reference to FIGS. 1 and 2, a walk-in steam decontamination apparatus for sterilizing or disinfecting items includes a cabinet 10 which defines an interior chamber 12. Items to be sterilized or disinfected are loaded into the chamber through an opening 16 in a front wall 18 of the cabinet. A horizontal sliding door assembly 20 is mounted to the front wall of the cabinet. The assembly includes a sliding door 22, a support system 24 for supporting the weight of the door during translation, and a horizontal guidance assembly 28, best shown in FIG. 2.

The support system 24 supports the weight of the door. The support system may be an overhead system as shown in FIG. 1, or a lower support system as shown in FIG. 2. The overhead support system is preferred because there is less likelihood of dirt becoming trapped in the support system and interfering with smooth operation of the door.

The guidance assembly 28 includes at least four pairs of rollers, at least two pairs of which are mounted to the door 22 so that they protrude vertically above the door and at least two pairs are mounted so that they protrude vertically below the door. The rollers are preferably mounted to a peripheral side wall 30 of the door. Specifically, a leading pair of rollers 32 and a trailing pair of rollers 34 are mounted to an upper panel 36 of the side wall 30. Similar pairs of leading and trailing rollers are mounted to a lower panel of the side wall. Alternatively, the rollers are mounted to other portions of the door, provided that they extend vertically above the door.

The upper rollers 32 and 34 slidingly engage an upper track or rail 38 which is securely mounted adjacent the front wall 18 of the cabinet. Specifically, the upper track 38 is mounted to the base of a horizontal mounting panel or bracket 40 which extends outwardly from the front wall 18 of the cabinet, although other mounting methods which maintain a fixed distance between the chamber opening 16 and the track are also contemplated. In the embodiment of FIG. 2, the mounting panel 40 is shown extending only part-way along the upper track 38 so that the positions of the rollers 32 and 34 can be better understood. It should be appreciated however, that the mounting panel preferably extends along the majority of the length of the upper track 38 for supporting the upper track. The lower rollers engage a similar, lower track 42.

Figure 3:
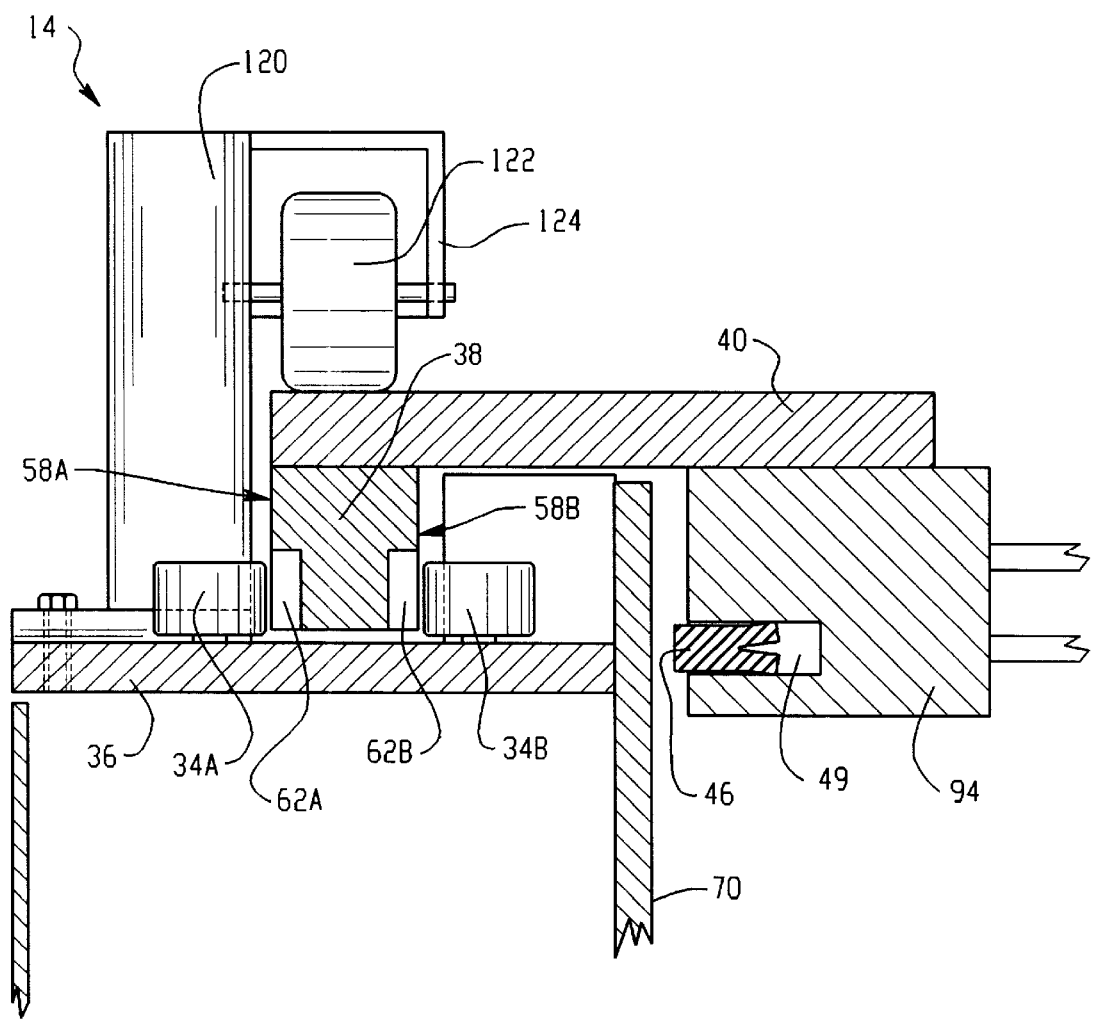
FIG. 3 is an enlarged side elevational view of the overhead mounting system of FIG. 1.

With reference also to FIG. 3, a seal 46 extends around the periphery of the opening 16 on the front wall 18 of the cabinet for sealingly engaging an interior face 48 of the door when the door is in the closed position. Preferably, the seal is an active seal which is mounted in a groove 49 in the front wall or other exterior surface.

Figure 4:
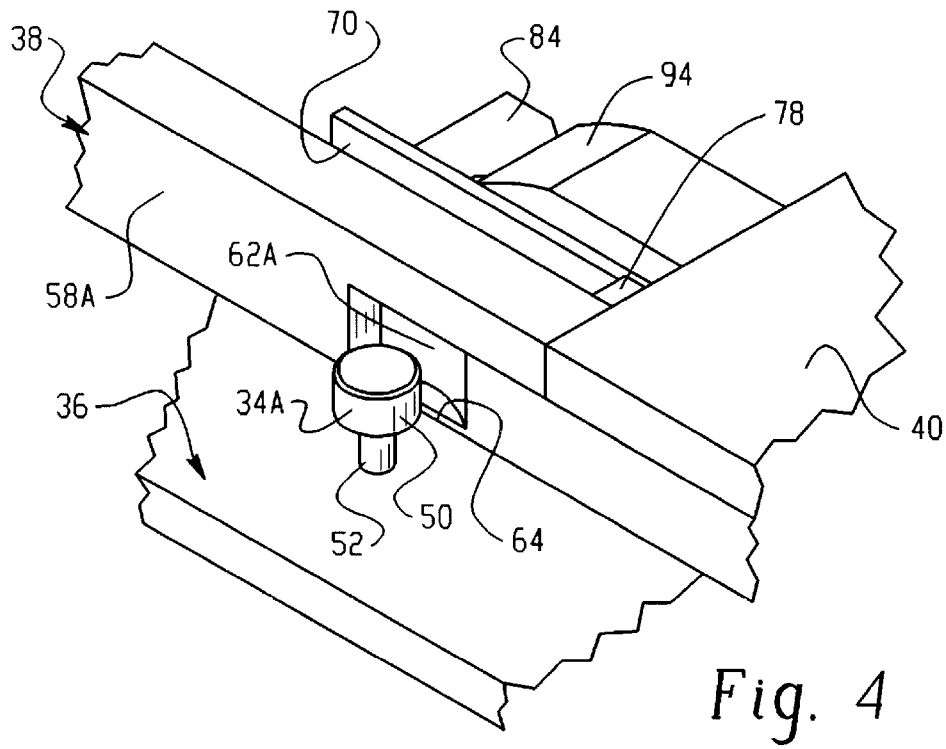
FIG. 4 is an exploded perspective view of the trailing rollers of FIG. 1.
Figure 5:
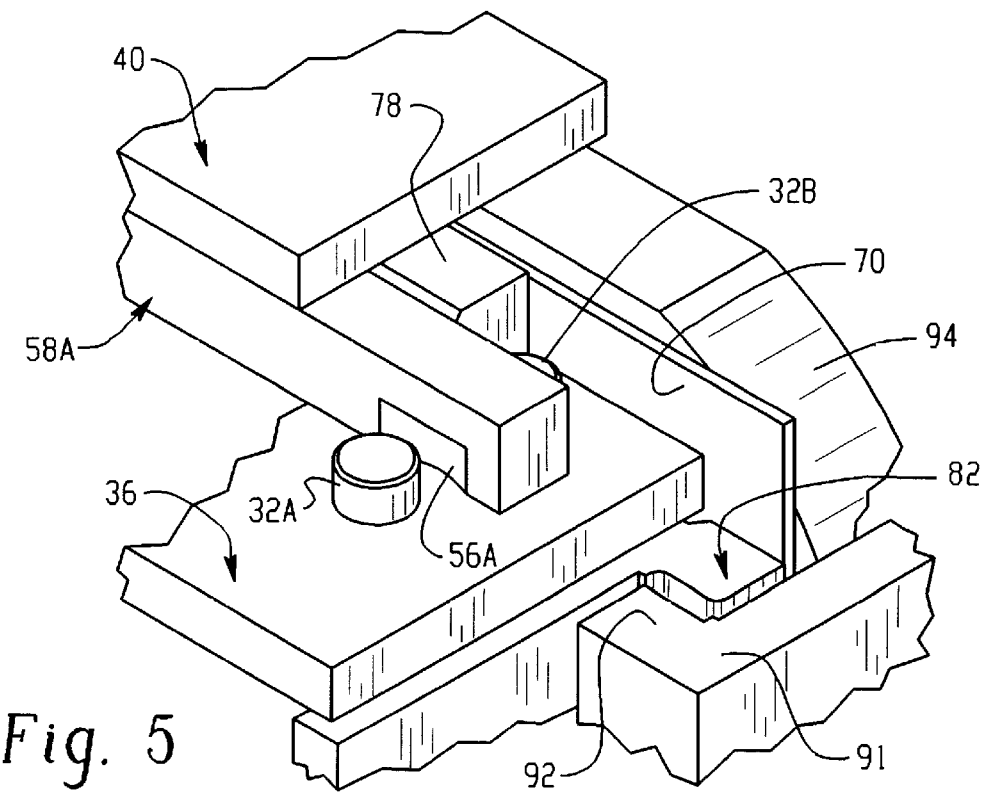
FIG. 5 is an enlarged perspective view of the leading rollers of FIG. 1.

With reference also to FIGS. 4 and 5, the upper leading and trailing pairs of rollers 32 and 34 are shown in greater detail. The leading pair of rollers 32 includes an outer leading roller 32A and an inner leading roller 32B, the inner roller being closer to the chamber opening than the outer roller. Similarly, the trailing rollers 34 include an outer trailing roller 34A and an inner trailing roller 34B. Each of the rollers includes a cylindrical portion 50 and an integral shaft 52 which extends axially from the cylindrical portion. The shafts are rotatably mounted to the upper panel 36 of the side wall of the door so that the cylinders rotate in a plane parallel to the top of the upper panel. The leading rollers 32A and 32B have shorter shafts 52 than those of the trailing rollers 34A and 34B and thus the cylindrical portions 50 engage the upper track at different heights.

Pairs of recesses or notches are defined in vertical sides of the upper track for receiving the rollers 32 and 34 when the door is fully closed. The recesses have a concave-shaped rear wall for accommodating an adjacent part of the cylindrical portion 50 of the respective roller. Specifically, a leading pair of recesses 56 includes an outer recess 56A and an equivalent inner recess 56B. The outer recess is defined in an outer vertical side 58A of the upper track, adjacent the point at which the leading rollers 32 stop when the door is in the closed position. The inner recess is similarly defined in an inner vertical side 58B. A trailing set of recesses 62A and 62B are defined in the inner and outer vertical sides 58A and 58B of the upper track adjacent where the trailing rollers 34A and 34B stop when the door is in the closed position. When the rollers are adjacent their respective recesses, the rollers can enter their respective recesses, giving the door 22 a limited amount of axial freedom of movement relative to the opening 16 in the chamber. This allows the door to move slightly in response to the fluctuations in pressure within the chamber. Other constructions that reduce the cross section of the upper track adjacent the location at which the rollers stop are also contemplated.

The trailing recesses 62A and 62B are positioned slightly higher on the vertical sides 58A and 58B of the upper track 36 than the leading recesses 56A and 56B. This leaves a small strip of land 64 defined by the each of the inner and outer vertical sides of the track beneath the corresponding upper trailing inner and outer recesses. As the door 22 is moved between the open position and the closed position, the leading rollers 32A and 32B engage the strips of land 64 beneath the corresponding recesses 62A and 62B and thus pass over the recesses without axial deviation. This prevents the door from undertaking axial movement until the door is fully closed. Damage to the seal 46, which could otherwise occur if the leading rollers were to enter the recesses 62 during closure or opening of the door, is thereby avoided. The extra height of the trailing rollers 34 allows these rollers to engage the trailing recesses 62 when the door is in the closed position. The lower rollers and recesses are similarly arranged, with the leading rollers engaging strips of land defined above the trailing recesses.

In an alternate embodiment, the respective heights of the upper and lower leading and trailing rollers are reversed, such that the upper leading rollers 32A and 32B have longer shafts 52 than the upper trailing rollers 34A and 34B. The vertical positions of the upper recesses 56 and 62 are also switched, so that the upper leading recesses 56 are slightly further from the door than the upper trailing recesses 62. In this embodiment, the leading upper rollers 32 engage a strip of land above the upper trailing recess during opening and closing of the door. The lower rollers and recesses may be similarly arranged, with the lower leading rollers engaging strips of land below the lower trailing recesses.

While the door guidance assembly 28 has been described as having both inner and outer recesses, it is contemplated that the upper inner recesses 56B and 62B and corresponding lower inner recesses, and optionally also the upper inner rollers 32B and 34B and corresponding lower inner rollers, may be eliminated. It is preferred, however, that both inner and outer recesses and rollers be present, to assist in guiding the door, maintaining the horizontal positioning of the door in the closed position, and providing greater axial freedom of movement of the door in the closed position.

Moreover, while the door guidance assembly 28 has been described with respect to two pairs of rollers on the top of the door and two on the bottom, it should be readily appreciated that more than four rollers may alternatively be employed, particularly for larger doors, and that the rollers need not be mounted in pairs. In this embodiment, the intermediate rollers and corresponding recesses are configured as for the trailing rollers and trailing recesses, so that the leading rollers travel on strips of land until reaching the leading recesses. The intermediate rollers do not enter adjacent recesses during opening and closing because the leading and trailing rollers guide the door.

Figure 6:
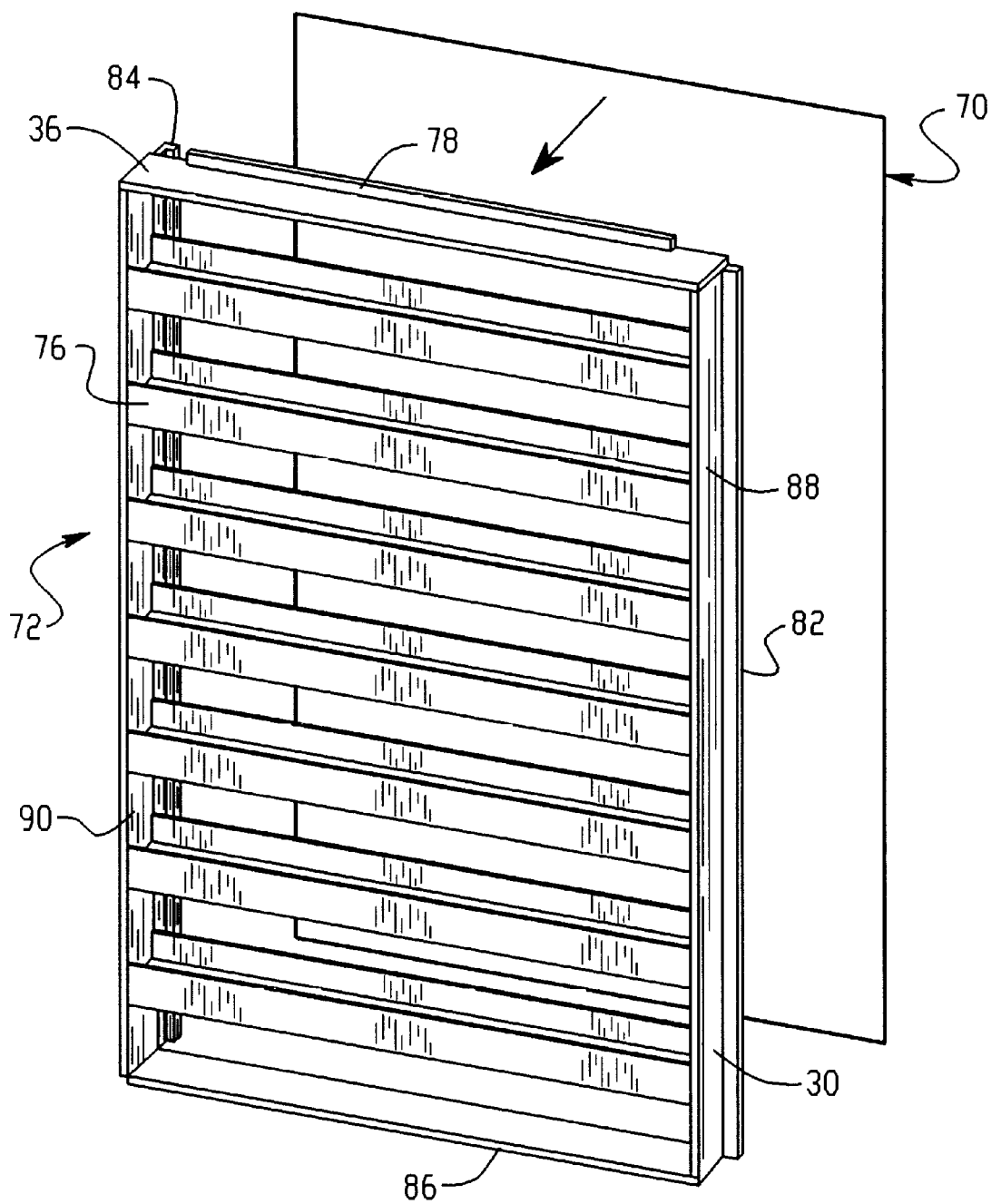
FIG. 6 is an expanded front perspective view of the door of FIGS. 1 and 2.
Figure 7:
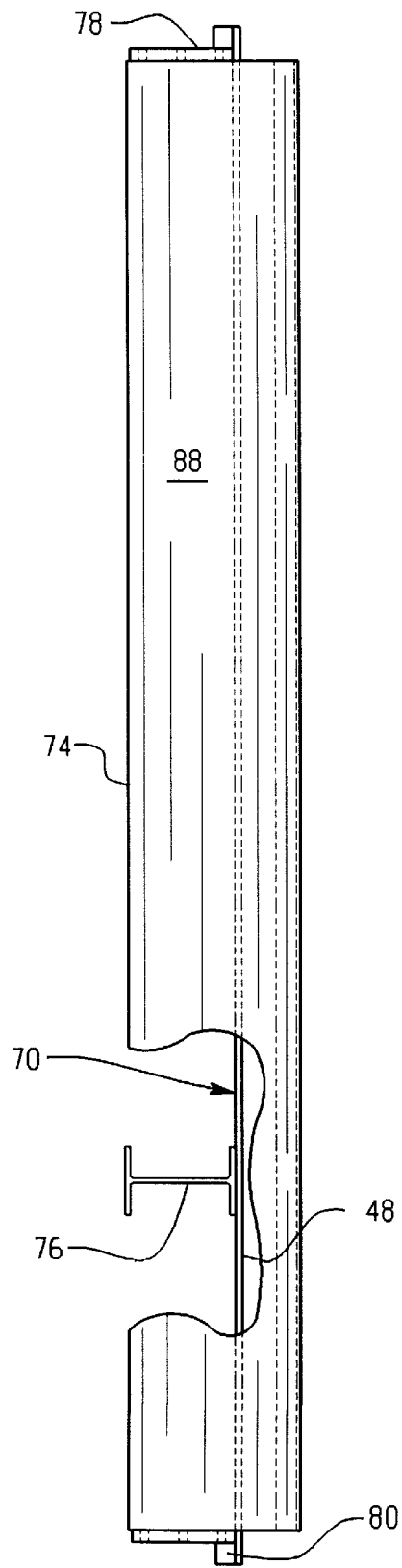
FIG. 7 is an enlarged side elevational view in partial section of the door of FIGS. 1 and 2.
Figure 8:
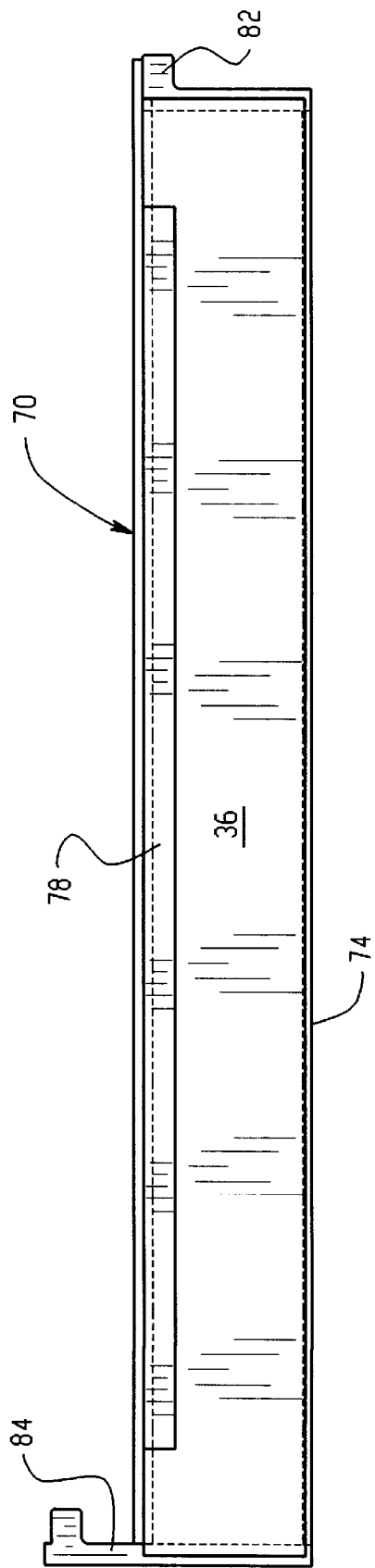
FIG. 8 is an enlarged top view of the door of FIGS. 1 and 2.

With reference also to FIGS. 6, 7, and 8, the door 22 includes a pressure plate 70, which is sized to cover the opening 16 and the seal 46, and a supporting framework 72, connected to the pressure plate, which defines the side wall 30 of the door. An outer wall of the door 74, best shown in FIGS. 1 and 2, is mounted to the outer edge of the supporting framework. The framework may include internal supporting braces 76. The supporting framework 72 holds the pressure plate 70 against flexing outward, across the opening when the door is closed. Specifically, upper and lower flanges 78, 80, and leading and trailing flanges 82 and 84, extend from the top panel 36, a bottom panel 86 and leading and trailing side panels 88 and 90 of the side wall 30, respectively. The flanges are configured to engage corresponding retaining members around the periphery of the opening 16. Specifically, the upper flange 78 extends vertically from the top panel 36. The upper track 38 defines a retaining member for the upper flange. The upper flange is thus slidingly received in a channel defined between the upper mounting panel 40 and the upper track. The leading flange 82 extends perpendicularly from the leading panel 88 of the supporting framework 72. The leading flange 82 is received by a vertical L-shaped retaining member 91 which extends from the front wall 18 of the cabinet. The L-shaped retaining member 91 includes a flange 92 which overlaps the flange 82. The trailing flange 84 is L-shaped extends rearwardly from the trailing side panel 90 of the side wall 30. The flange 84 engages a back plate 94 when the door is in the closed position. The back plate is mounted to the front wall 18 of the cabinet around the periphery of the opening. The lower flange extends vertically from the lower panel 86. The lower track 42 defines a retaining member for the lower flange 80. The lower flange is thus received by a channel defined between the lower track 42 and lower mounting panel, in similar manner to the upper flange 78.

Thus, when the door is the closed position, each side of the door is retained by a corresponding retaining member. When the seal 46 is activated, the door is pushed slightly outward from the opening 16 in the cabinet and each of the flanges 78, 80, 82 and 84 engages the respective retaining member. The upper flange 78 engages the inner surface 58B of the upper track 38. The leading flange 82 engages the retaining member flange 92. The trailing flange 84 engages the rear surface of the back plate 94 and the lower flange engages the lower track 42 in a similar manner to the upper flange 78. In this way, all four sides of the door are evenly retained. The outer rollers 32A and 32B move outwardly from their respective recesses accordingly. When the pressure inside the chamber 12 is reduced, such as when a vacuum is drawn, the door moves slightly toward the chamber opening 16 and the flanges are disengaged slightly from their respective retaining members. The outer rollers 32A and 34A are drawn into their respective recesses 56A and 62A.

With reference once more to FIGS. 1 and 3, the overhead support system 24 includes two or more identical support assemblies, namely a leading support assembly 112, mounted to the door 22 adjacent to the leading panel 88, and a trailing support assembly 114, mounted to the door adjacent to the trailing panel 90. Each of the support assemblies 112, 114 is rigidly connected to the door by a vertically extending bracket 120. The bracket 120 is releasably connected to the top panel 36 by any convenient means, such as screws or bolts. A supporting wheel or roller 122 is rotatably supported by an inner leg 124 of the U-shaped bracket. The supporting wheel 122 may be mounted within a housing 128 connected to the leg 124. A similar support assembly 112, 114 is mounted to either end of the top of the door.

The wheels 122 run on an upper surface 130 of the mounting panel 40. The weight of the door is thus supported on the mounting panel. As the door is opened and closed, the wheels 122 move along the upper surface 130.

Figure 9:
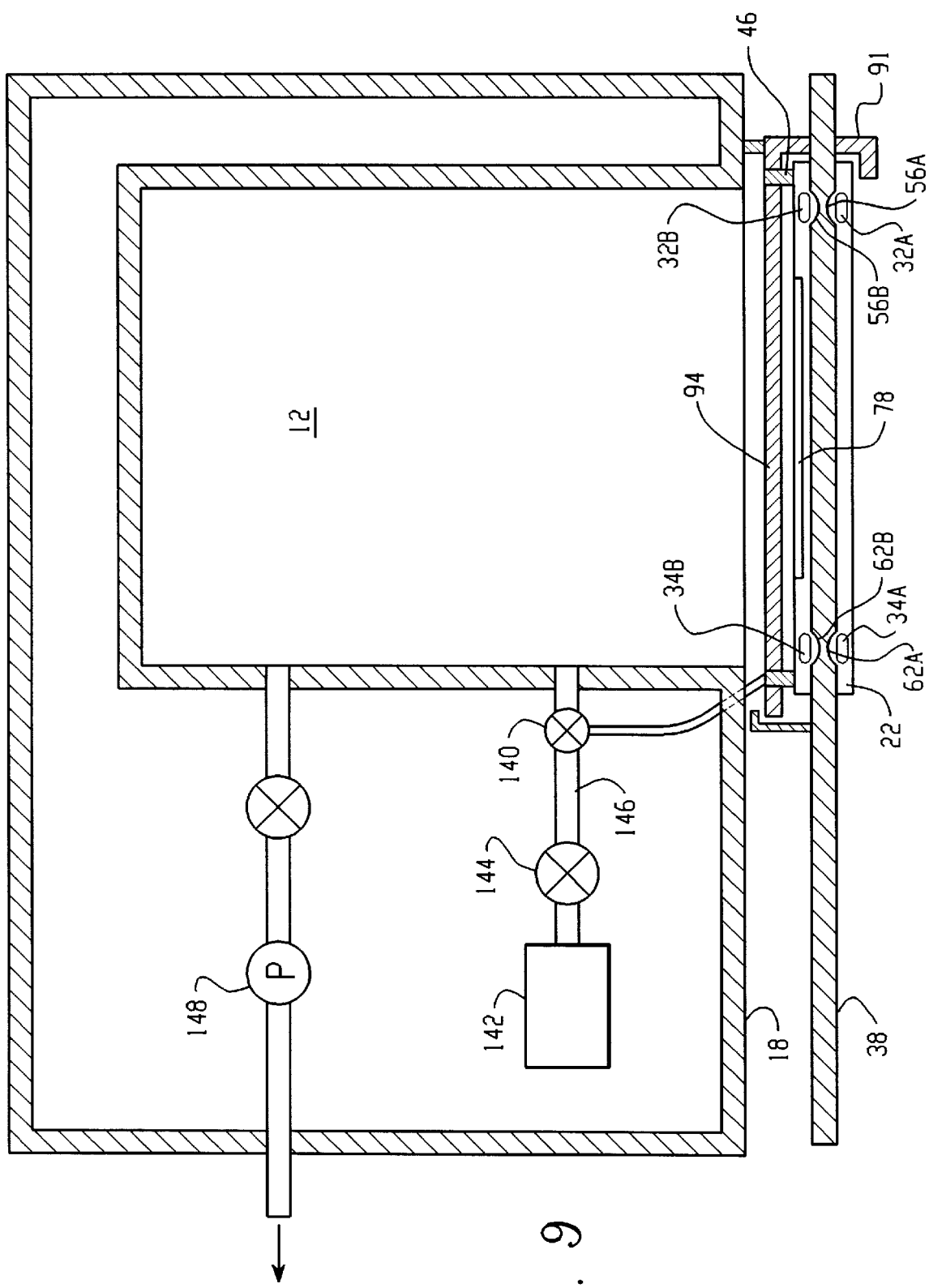
FIG. 9 is a top view in partial section of the steam sterilizer of FIG. 1.

With reference once more to FIGS. 1 and 3 and reference also to FIG. 9, the sterilizing or disinfecting apparatus is operated by first loading items through the opening 16 and into the chamber 12, while the door 22 is in the open position. The door is then moved into the closed position. This may be done manually, by pushing the door so that it moves along the tracks 38 and 42, or by using a motorized system (not shown). Once the door is closed, the seal 46 is activated. The seal is activated by opening a valve 140 connected to a source of steam, such as a steam generator 142, to supply pressurized steam into the interior of the seal, causing it to expand outward from the groove. This pushes the door outward. Outward movement of the door is limited by the engagement of the flanges 78, 80, 82, and 84, with their corresponding retaining members 38, 42, 91, and 94. The inner rollers 32B and 34B enter their corresponding recesses 56B and 62B so that the rollers are not placed under stress by the outward movement of the door. The steam generator 142 supplies the chamber with steam by opening a valve 144 in a conduit 146 connected between the generator and the chamber. The added pressure of the steam may cause further outward movement of the door, causing the inner rollers 32B and 34B to move slightly further into their respective recesses.

At the end of a sterilization or disinfection cycle, a source of vacuum, such as a vacuum pump 148 applies a vacuum to the chamber 12 to draw the steam out of the chamber. The reduced pressure also draws the door plate so into closer engagement with the seal 46 which pulls the attached framework 72 and rollers closer to the opening. The outer rollers 32A and 34A enter the corresponding outer recesses 56A and 62A to avoid stresses on the rollers. The depths of the recesses are selected so that the rollers can enter their respective recesses as the door moves without placing a stress on the rollers.

In some installations, it is advantageous for the door to slide open to the right. To convert the door from a left-to-right closing door to a right-to-left closing door, the support assemblies 112, 114 are simply unbolted and the door rotated through 180 degrees so that the base of the door becomes the top. The support assemblies 112, 114 are then mounted to the top of the door. With the door mounted in the reversed position, the leading rollers 32A and 32B are positioned at the lower left of the door and the leading rollers from the base of the door are positioned at the top left of the door. The door is then ready to move toward the left when closing.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A sterilization or disinfection apparatus comprising:
   a housing which defines an interior chamber and an opening;
   a door having an interior face sized to seal the opening, an outer face, a leading edge, a trailing edge, and a pair of opposite sides;
   a guidance assembly for guiding the door between an open position, in which items to be sterilized or disinfected are capable of being loaded into the chamber, and a closed position, in which the door covers the opening, the guidance assembly including:
      two leading sets of rollers rotatably mounted by shaft portions of each of the rollers adjacent the leading edge of the door, a first set of the leading sets of rollers mounted to a first side of the door and a second set of the leading sets of rollers mounted to a second side of the door, each of the leading sets of rollers including a leading outer roller and a leading inner roller;
      two trailing sets of rollers rotatably mounted by shaft portions of each of the rollers adjacent the trailing edge of the door, a first set of the trailing sets of rollers mounted to the first side of the door and a second set of the trailing sets of rollers mounted to the second side of the door, each of the trailing sets of rollers including a trailing outer roller and a trailing inner roller, the shaft portion of one of the first set trailing outer roller and the first set leading outer roller being longer than the other, the shaft portion of one of the second set trailing outer roller and the second set leading outer roller being longer than the other;
      a first track mounted adjacent the first side of the door, the first track including an outer surface, the outer leading and trailing rollers mounted to the first side of the door engaging the outer surface of the first track;
      a second track mounted adjacent the second side of the door, the second track including an outer surface, the outer leading and trailing rollers mounted to the second side of the door engaging the outer surface of the second track;
      a first leading recess defined in the outer surface of the first track for receiving the leading outer roller mounted to the first side of the door when the door is in the closed position;
      a first trailing recess defined in the outer surface of the first track for receiving the trailing outer roller mounted to the first side of the door when the door is in the closed position;
      a second leading recess defined in the outer vertical surface of the second track for receiving the leading outer roller mounted to the second surface of the door when the door is in the closed position; and,
      a second trailing recess defined in the outer vertical surface of the second track for receiving the trailing outer roller mounted to the second surface of the door when the door is in the closed position.

2. The system of claim 1, wherein:
   the first trailing recess is vertically positioned such that the first set leading outer roller does not enter the first trailing recess as the door is moved between the open position and the closed position; and,
   the second trailing recess is vertically positioned such that the second set leading outer roller does not enter the second trailing recess as the door is moved between the open position and the closed position.

3. The apparatus of claim 1, further including:
   a seal between the door and the housing surrounding the opening to the chamber which selectively seals against the door, the guidance assembly maintaining a space between the door and the seal when the door is moving between the open and closed positions.

4. The apparatus of claim 3, further including:
   a suspension system which carries the weight of the door when the door is moving between the open position and the closed position.

5. The system of claim 1, further including:
   a third leading recess defined in the inner surface of the first track for receiving the first set leading inner roller when the door is in the closed position;
   a third trailing recess defined in the inner surface of the first track for receiving the first set trailing inner roller when the door is in the closed position;
   a fourth leading recess defined in the inner vertical surface of the second track for receiving the second set leading inner roller when the door is in the closed position; and,
   a fourth trailing recess defined in the inner vertical surface of the second track for receiving the second set trailing inner roller when the door is in the closed position.

6. The system of claim 5, wherein:
   the third leading recess and the third trailing recess have a sufficient depth that when the inner rollers enter the recesses, a flange extending from an adjacent first side of the door engages the inner vertical surface of the first track; and,
   the fourth leading recess and the fourth trailing recess have a sufficient depth that when the inner rollers enter the recesses, a flange extending from an adjacent second side of the door engages the inner vertical surface of the second track.

7. The system of claim 6, wherein the apparatus further includes:

a leading retaining member which engages a leading flange extending from the leading edge of the door when the inner rollers enter the inner recesses; and, a trailing retaining member which engages a trailing flange extending from the trailing edge of the door when the inner rollers enter the inner recesses.

8. A system which guides a door horizontally between an open position and a closed position, in which a chamber opening is sealed, the system comprising:

two leading rollers rotatably mounted to the door by shaft portions of each of the leading rollers adjacent a leading edge of the door, an upper leading roller of the two leading rollers mounted to an upper surface of the door and a lower leading roller of the two leading rollers mounted to a lower surface of the door;

two trailing rollers rotatably mounted to the door by shaft portions of each of the trailing rollers adjacent a trailing edge of the door, an upper trailing roller of the two rollers mounted to an upper surface of the door and a lower trailing roller of the two rollers mounted to a lower surface of the door, the shaft portion of a first one of the upper trailing roller and the upper leading roller being longer than the shaft portion of a second one of the upper trailing roller and the upper leading roller, and the shaft portion of a first one of the lower trailing roller and the lower leading roller being longer than the shaft portion of a second one of the lower trailing roller and the lower leading roller;

an upper track mounted adjacent an upper peripheral edge of the opening, the leading and trailing upper rollers engaging the upper track;

a lower track mounted adjacent a lower peripheral edge of the opening, the leading and trailing lower rollers engaging the lower track;

an upper leading recess defined in the upper track for receiving the upper leading roller when the door is in closed position;

an upper trailing recess defined in the upper track for receiving the upper trailing roller when the door is in a the closed position, the upper trailing recess being vertically positioned such that the upper leading roller does not enter the upper trailing recess as the door is moved between the open position and the closed position;

a lower leading recess defined in the lower track for receiving the lower leading roller when the door is in the closed position; and, a lower trailing recess defined in the lower track for receiving the lower trailing roller when the door is in the closed position, the lower trailing recess being vertically positioned such that the lower leading roller does not enter the lower trailing recess as the door is moved between the open position and the closed position.

9. The system of claim 8, wherein:

the first one of the upper trailing roller and the upper leading roller is the upper trailing roller and the upper trailing recess is vertically positioned in an outer vertical surface of the upper track such that the upper leading roller engages a strip of land below the recess on the outer vertical surface of the upper track as the door is moved between the open position and the closed position; and, the first one of the lower trailing roller and the lower leading roller is the lower trailing roller and the lower trailing recess is vertically positioned in an outer vertical surface of the lower track such that the lower leading roller engages a strip of land above the recess on the outer vertical surface of the lower track as the door is moved between the open position and the closed position.

10. The system of claim 8, further including:

two additional leading rollers rotatably mounted to the door by shaft portions of each of the additional leading rollers adjacent a leading edge of the door, an upper leading roller of the two additional leading rollers mounted to the upper surface of the door and a lower leading roller of the two additional leading rollers mounted to the lower surface of the door;

two additional trailing rollers rotatably mounted to the door by shaft portions of each of the additional trailing rollers adjacent the trailing edge of the door, an upper trailing roller of the two additional rollers mounted to the upper surface of the door and a lower trailing roller of the two additional rollers mounted to the lower surface of the door, the shaft portion of a first one of the additional upper trailing and leading rollers being longer than the shaft portion of a second one of the additional upper trailing and leading rollers, and the shaft portion of a first one of the additional lower trailing and leading rollers being longer than the shaft portion of a second one of the additional lower trailing and leading rollers, the additional rollers being inner rollers which are mounted closer to the chamber than the other rollers, the other rollers being outer rollers;

the upper track includes an outer vertical surface and an inner vertical surface, the inner vertical surface of the upper track being closer to the chamber than the outer vertical surface, the outer leading and trailing upper rollers engaging the outer vertical surface of the upper track and the inner leading and trailing upper rollers engaging the inner vertical surface of the upper track, the upper recesses being defined in the outer vertical surface of the upper track; and, the lower track includes an outer vertical surface and an inner vertical surface, the inner vertical surface of the lower track being closer to the chamber than the outer vertical surface, the outer leading and trailing lower rollers engaging the outer vertical surface of the lower track and the inner leading and trailing lower rollers engaging the inner vertical surface of the lower track, the lower recesses being defined in the outer vertical surface of the lower track.

11. The system of claim 10, wherein:

the shaft portion of a first one of the upper trailing inner roller and the upper leading inner roller is longer than the shaft portion of a second one of the upper trailing inner roller and the upper leading inner roller, and the shaft portion of a first one of the lower trailing inner roller and the lower leading inner roller is longer than the shaft portion of a second one of the lower trailing inner roller and the lower leading inner roller;

an upper leading recess is defined in the inner vertical surface of the upper track for receiving the upper leading inner roller when the door is in the closed position;

an upper trailing inner recess defined in the inner vertical surface of the upper track for receiving the upper trailing inner roller when the door is in the closed position, the upper trailing recess being vertically positioned such that the upper leading inner roller does not enter the upper trailing inner recess as the door is moved between the open position and the closed position;

a lower leading inner recess is defined in the inner vertical surface of the lower track for receiving the lower leading inner roller when the door is in a closed position;

a lower trailing inner recess is defined in the inner vertical surface of the lower track for receiving the lower trailing inner roller when the door is in the closed position, the lower trailing inner recess being vertically positioned such that the lower leading inner roller does not enter the lower trailing inner recess as the door is moved between the open position and the closed position.

12. The system of claim 11, wherein:

the first one of the upper trailing inner roller and the upper leading inner roller is the upper trailing inner roller and wherein the upper trailing recess is vertically positioned such that the upper leading inner roller engages a strip of land above the recess on the inner vertical surface of the upper track as the door is moved between the open position and the closed position; and, the first one of the lower trailing inner roller and the lower leading inner roller is the lower trailing inner roller and wherein the lower trailing recess is vertically positioned such that the lower leading inner roller engages a strip of land above the recess on the inner vertical surface of the lower track as the door is moved between the open position and the closed position.

13. The system of claim 8, wherein:

the upper surface of the door defines a first flange and the lower surface of the door defines a second flange, the first flange engaging an inner surface of the upper track and the second flange engaging an inner surface of the lower track when the door is in the closed position, the upper and lower tracks limiting outward movement of the door.

14. The system of claim 13, wherein:

a leading surface of the door defines a third flange, and a trailing surface of the door defines a fourth flange, a leading retaining member adjacent a leading peripheral side of the opening in the chamber engaging the third flange when the door is in the closed position and a trailing retaining member adjacent a trailing peripheral edge of the opening in the chamber engaging the fourth flange when the door is in the closed position, such that outward movement of the door is restrained on four sides of the door.

15. A method of guiding a sliding door between an open position, in which access is provided to the interior of a steam cabinet through an opening defined in the cabinet, and a closed position, in which the opening is covered by the door, the method comprising the steps of:

rolling a first upper leading roller which is rotatably connected to the door adjacent to an upper leading end of the door and a first upper trailing roller which is rotatably connected to the door adjacent to an upper trailing end of the door, along an outer surface of a horizontal upper track until the first upper leading roller engages a leading recess defined in the outer surface of the upper track and the first upper trailing roller engages a trailing recess defined in the outer surface of the upper track, the step of rolling the first upper leading and trailing rollers including:

rolling the first upper leading roller across a strip of land defined by the outer surface of the upper track extending across the trailing recess in a direction of travel, the strip of land engaging a portion of the first upper leading roller so that the first upper leading roller is not received by the trailing recess;

simultaneously rolling a first lower leading roller which is rotatably connected to the door adjacent to an lower leading end of the door and a first lower trailing roller which is rotatably connected to the door adjacent to an lower trailing end of the door, along an outer surface of a lower track until the first lower leading roller engages a leading recess defined in the outer surface of the lower track and the first lower trailing roller engages a trailing recess defined in the lower track, the step of rolling the first lower leading and trailing rollers including:

rolling the first lower leading roller across a strip of land defined by the outer surface of the lower track extending across the trailing recess in a direction of travel, the land engaging a portion of the first lower leading roller so that the lower leading roller is not received by the trailing recess.

16. The method of claim 15, further including:

simultaneously rolling a second upper leading roller which is rotatably connected to the door adjacent to an upper leading end of the door closer to the opening than the first upper leading roller and a second upper trailing roller which is rotatably connected to the door adjacent to an upper trailing end of the door closer to the opening than the first upper trailing roller, along an inner surface of the upper track; and, simultaneously rolling a second lower leading roller which is rotatably connected to the door adjacent to an lower leading end of the door closer to the opening than the first lower leading roller and a lower trailing roller which is rotatably connected to the door adjacent to an lower trailing end of the door closer to the opening than the first lower trailing roller, along an inner surface of the lower track.

17. The method of claim 15, further including:

selectively engaging a first flange on an upper surface of the door with an inner surface of the upper track; and, selectively engaging a second flange on a lower surface of the door with an inner surface of the lower track.

18. The method of claim 17, further including:

selectively engaging a third flange on a leading edge of the door with a leading retaining member; and selectively engaging a fourth flange on a trailing edge of the door with a trailing retaining member, the leading and trailing retaining members limiting outward movement of the leading an trailing edges of the door when the door is in the closed position.

19. The method of claim 17, wherein the steps of engaging a first flange and a second flange include:

activating a seal between the cabinet and the door, the seal pushing the door outward from the chamber.

20. The method of claim 19, wherein the steps of engaging a first flange and a second flange further include:

introducing steam into the chamber, the steam providing an outward pressure on the door.

21. The method of claim 15, further including:

drawing a vacuum in the chamber, the vacuum pulling the door towards the chamber such that the rollers enter the recesses.

22. A method of sealing a chamber opening comprising the steps of:

guiding a door from an open position, in which access to the opening is provided, to a closed position, in which the door covers the opening including:

rolling a first upper leading roller which is rotatably connected to the door adjacent to an upper leading end of the door and a first upper trailing roller which is rotatably connected to the door adjacent to an upper trailing end of the door, along an outer surface of a horizontal upper track until the first upper leading roller engages a leading recess defined in the outer surface of the upper track and the first upper trailing roller engages a trailing recess defined in the outer surface of the upper track, the step of rolling the first upper leading and trailing rollers including:

rolling the first upper leading roller across a strip of land defined by the outer surface of the upper track adjacent the trailing recess, the strip of land engaging a portion of the first upper leading roller so that the first upper leading roller is not received by the trailing recess;

simultaneously rolling a first lower leading roller which is rotatably connected to the door adjacent to an lower leading end of the door and a first lower trailing roller which is rotatably connected to the door adjacent to an lower trailing end of the door, along an outer surface of a horizontal lower track until the first lower leading roller engages a leading recess defined in the outer surface of the lower track and the first lower trailing roller engages a trailing recess defined in the lower track, the step of rolling the first lower leading and trailing rollers including:

rolling the first lower leading roller across a strip of land defined by the outer surface of the lower track adjacent the trailing recess, the land engaging a portion of the first lower leading roller so that the lower leading roller is not received by the trailing recess;

engaging a first flange on an upper surface of the door with an inner surface of the upper track;

engaging a second flange on a lower surface of the door with a rear surface of the lower track; and, activating a seal to seal the door to the periphery of the opening.

* * * * *